US009486252B2

(12) United States Patent
McCarthy et al.

(10) Patent No.: US 9,486,252 B2
(45) Date of Patent: Nov. 8, 2016

(54) SPINAL CORRECTION SYSTEM AND METHOD

(71) Applicant: Medtronic, Inc., Warsaw, IN (US)

(72) Inventors: Richard E McCarthy, Little Rock, AR (US); Brian A. Butler, Atoka, TN (US); Joshua W. Simpson, Collierville, TN (US); Gary S. Lindemann, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 156 days.

(21) Appl. No.: 14/151,042

(22) Filed: Jan. 9, 2014

(65) Prior Publication Data
US 2015/0190178 A1    Jul. 9, 2015

(51) Int. Cl.
 *A61B 17/70*    (2006.01)
(52) U.S. Cl.
 CPC ......... *A61B 17/707* (2013.01); *A61B 17/7049* (2013.01); *A61B 17/7052* (2013.01)
(58) Field of Classification Search
 CPC .................. A61B 17/7049; A61B 17/7052
 USPC ........................................ 606/250–251, 278
 See application file for complete search history.

(56) References Cited

U.S. PATENT DOCUMENTS

| | | | | |
|---|---|---|---|---|
| 5,413,576 A | * | 5/1995 | Rivard ............... | A61B 17/7047 606/250 |
| 5,514,132 A | * | 5/1996 | Csernatony ........ | A61B 17/7001 606/276 |
| 5,989,251 A | * | 11/1999 | Nichols .............. | A61B 17/7049 606/246 |
| 7,338,490 B2 | * | 3/2008 | Ogilvie .............. | A61B 17/7053 606/276 |
| 7,485,133 B2 | * | 2/2009 | Cannon .............. | A61B 17/7056 606/246 |
| 8,034,082 B2 | * | 10/2011 | Lee .................... | A61B 17/7052 606/250 |
| 8,721,688 B1 | * | 5/2014 | Wang ................. | A61B 17/7056 606/250 |
| 8,888,819 B2 | * | 11/2014 | Frasier ............... | A61B 17/701 606/264 |
| 8,926,673 B2 | * | 1/2015 | Clement ............. | A61B 17/7001 606/276 |
| 9,107,703 B2 | * | 8/2015 | Torres ................ | A61B 17/7052 |
| 9,125,691 B2 | * | 9/2015 | Gunn ................. | A61B 17/7049 |

(Continued)

*Primary Examiner* — Ellen C Hammond
*Assistant Examiner* — Stuart S Bray

(57) ABSTRACT

A spinal construct comprises a longitudinal element including at least one part configured for connecting to tissue of a rib cage. A member is connected with the longitudinal element and configured for connection with a spinal implant fixed with vertebrae. Systems and methods are disclosed.

13 Claims, 7 Drawing Sheets

(56) References Cited

U.S. PATENT DOCUMENTS

| | | | | |
|---|---|---|---|---|
| 9,211,144 B2* | 12/2015 | Stauber | | A61B 17/7049 |
| 2005/0228378 A1* | 10/2005 | Kalfas | | A61B 17/705 |
| | | | | 606/252 |
| 2006/0058789 A1* | 3/2006 | Kim | | A61B 17/7049 |
| | | | | 606/914 |
| 2006/0282073 A1* | 12/2006 | Simanovsky | | A61B 17/707 |
| | | | | 606/282 |
| 2008/0086115 A1* | 4/2008 | Stoklund | | A61B 17/8076 |
| | | | | 606/1 |
| 2008/0109039 A1* | 5/2008 | Michielli | | A61B 17/7049 |
| | | | | 606/251 |
| 2009/0112207 A1* | 4/2009 | Walker | | A61B 17/7016 |
| | | | | 606/57 |
| 2009/0259256 A1* | 10/2009 | Miller | | A61B 17/705 |
| | | | | 606/250 |
| 2009/0287253 A1* | 11/2009 | Felix | | A61B 17/7058 |
| | | | | 606/278 |
| 2010/0004697 A1* | 1/2010 | Fortin | | A61B 17/66 |
| | | | | 606/86 R |
| 2010/0137913 A1* | 6/2010 | Khatchadourian | | A61B 17/7014 |
| | | | | 606/258 |
| 2010/0217271 A1* | 8/2010 | Pool | | A61B 17/7004 |
| | | | | 606/90 |
| 2011/0087288 A1* | 4/2011 | Stevenson | | A61B 17/7037 |
| | | | | 606/250 |
| 2012/0016420 A1* | 1/2012 | Naraghi | | A61B 17/7064 |
| | | | | 606/250 |
| 2012/0035656 A1* | 2/2012 | Pool | | A61B 17/7004 |
| | | | | 606/246 |
| 2012/0035659 A1* | 2/2012 | Barrus | | A61B 17/7049 |
| | | | | 606/251 |
| 2012/0158065 A1* | 6/2012 | Jouve | | A61B 17/7001 |
| | | | | 606/276 |
| 2013/0030470 A1* | 1/2013 | Karas | | A61B 17/1757 |
| | | | | 606/264 |
| 2013/0096614 A1* | 4/2013 | Zhang | | A61B 17/7068 |
| | | | | 606/250 |
| 2013/0123851 A1* | 5/2013 | Seme | | A61B 17/70 |
| | | | | 606/250 |
| 2013/0150889 A1* | 6/2013 | Fening | | A61B 17/7022 |
| | | | | 606/257 |
| 2013/0268003 A1* | 10/2013 | Hwang | | A61B 17/7052 |
| | | | | 606/251 |
| 2014/0046372 A1* | 2/2014 | Ibrahim | | A61B 17/8605 |
| | | | | 606/250 |
| 2014/0066985 A1* | 3/2014 | Asaad | | A61B 17/7052 |
| | | | | 606/252 |
| 2014/0222074 A1* | 8/2014 | Rathbun | | A61B 17/7014 |
| | | | | 606/258 |
| 2014/0277147 A1* | 9/2014 | Alexander | | A61B 17/7014 |
| | | | | 606/259 |
| 2014/0288603 A1* | 9/2014 | Black | | A61B 17/7049 |
| | | | | 606/252 |
| 2014/0296918 A1* | 10/2014 | Fening | | A61B 17/7016 |
| | | | | 606/258 |
| 2014/0316467 A1* | 10/2014 | Siegal | | A61B 17/7062 |
| | | | | 606/249 |
| 2015/0119941 A1* | 4/2015 | Daniels | | A61B 17/7052 |
| | | | | 606/270 |
| 2015/0134002 A1* | 5/2015 | Khatchadourian | | A61B 17/7014 |
| | | | | 606/258 |
| 2015/0190178 A1* | 7/2015 | McCarthy | | A61B 17/707 |
| | | | | 606/276 |
| 2015/0305780 A1* | 10/2015 | Carlson | | A61B 17/7049 |
| | | | | 606/254 |
| 2015/0335363 A1* | 11/2015 | Walsh | | A61B 17/707 |
| | | | | 606/249 |
| 2016/0015430 A1* | 1/2016 | Buttermann | | A61B 17/7032 |
| | | | | 606/276 |

* cited by examiner

SPINAL CORRECTION SYSTEM AND METHOD

TECHNICAL FIELD

The present disclosure generally relates to medical devices for the treatment of musculoskeletal disorders, and more particularly to a surgical system for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction discectomy, laminectomy, fusion, fixation and implantable prosthetics. Correction treatments used for positioning and alignment of vertebrae may employ implants, such as for example, spinal constructs. The spinal constructs, which may include rods and bone screws, are manipulated with surgical instruments for engagement with vertebrae to position and align one or more vertebrae. This disclosure describes improvements over these prior art technologies.

SUMMARY

In one embodiment, a spinal construct is provided. The spinal construct comprises a longitudinal element including at least one part configured for connecting to tissue of a rib cage. A member is connected with the longitudinal element and configured for connection with a spinal implant fixed with vertebrae. In some embodiments, systems and methods are provided.

In one embodiment, a method for treating a spine is provided. The method comprises fastening at least one bone fastener to vertebrae; connecting a spinal implant with the at least one bone fastener; providing a spinal construct comprising a longitudinal element including at least one part, and a member extending between a first end connected with the longitudinal element and a second end; engaging the second end with the spinal implant; and connecting the at least one part with tissue of a rib cage.

BRIEF DESCRIPTION OF THE DRAWINGS

The present disclosure will become more readily apparent from the specific description accompanied by the following drawings, in which.

DETAILED DESCRIPTION

Figure 1:
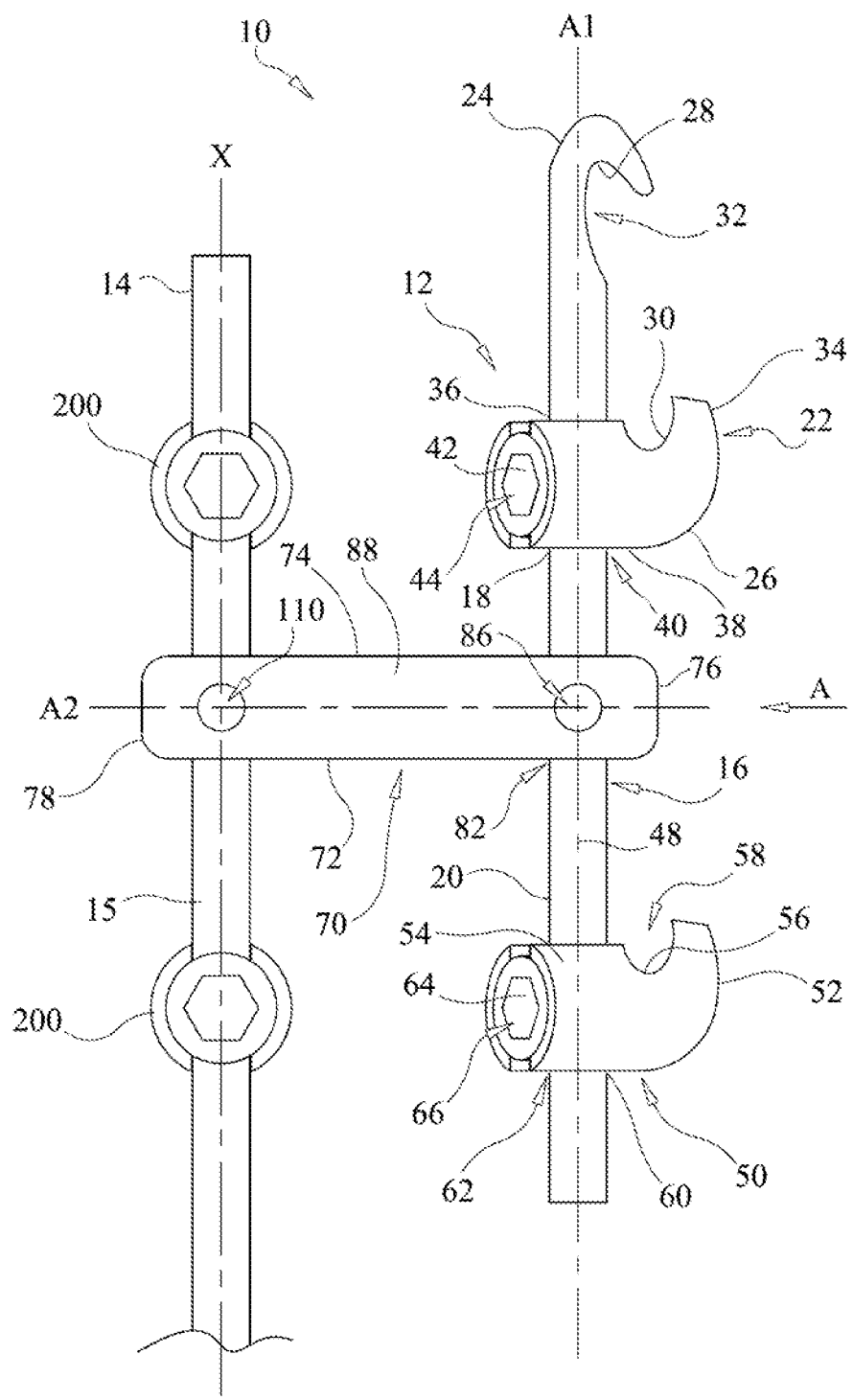
FIG. 1 is a plan view of components of one embodiment of a system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder.

In one embodiment, the surgical system includes an outrigger construct attached to tissue of a rib cage and a main construct, such as, for example, bone fasteners and/or spinal rods fixed with vertebrae. In one embodiment, the outrigger construct is attached to tissue adjacent a scapula and muscle of a patient. This configuration resists and/or prevents the outrigger construct and/or the main construct from protruding and/or causing undesirable irritation to the patient, for example, through the skin of the patient. In one embodiment, the outrigger construct is surgically implanted with tissue beneath the scapula and beneath the muscle relative to the skin of the patient. In one embodiment, the outrigger construct is surgically implanted unilaterally relative to a spine. In one embodiment, the outrigger construct is surgically implanted bilaterally relative to a spine. In one embodiment, the outrigger construct is connected with spinal rods via a sliding connection mechanism. In one embodiment, the outrigger construct is hooked to a rib of a rib cage connecting the ribs to the main construct. In some embodiments, the outrigger construct provides support to the bone fasteners, such as, for example, cephalad screws and/or allows a patient, such as, for example, a child, to grow.

In one embodiment, the surgical system includes a short section of a longitudinal element, such as, for example, a rod. In some embodiments, the rod includes a first hook on a first end and a second hook that is slidable relative to the first hook. In one embodiment, the first and second hooks each include a hook portion forming a hook claw to capture a rib of a rib cage therewith. In one embodiment, the second hook includes an inner surface defining an opening configured for disposal about the rod such that the second hook is translatable along the rod relative to the first hook. In one embodiment, the second hook is detachably engageable with the rod via a set screw in a selected position.

In one embodiment, a surgical system includes a sliding connector connected to a main construct at a first end and connected to the rod at a second end. In some embodiments, the main construct is employed with a method that allows for the natural growth of the spine and correction of the spine. In some embodiments, the main construct includes a track system that includes rods partially fixated to the spine. In some embodiments, this configuration allows the track system to grow with the patient thereby preventing rod breakage.

In one embodiment, a first end of the sliding connector includes an opening extending through a medial side of the sliding connector. The medial side opening is configured for disposal of the main construct. In one embodiment, the medial side opening allows for positioning the outrigger construct in a revision surgery. In one embodiment, a second end or lateral side of the sliding connector includes an inner surface defining an enclosed opening such that the rod is translatable through the enclosed opening relative to the connector. In one embodiment, the inner surface of the enclosed opening includes an insert or layer of material configured to resist and/or prevent degradation and wear and provide reduced friction between the rod and inner surface such that translation of the connector along the rod is met with low resistance. In one embodiment, the medial side opening captures the rod and allows the rod to translate relative to the connector to provide flexibility to the main construct. In one embodiment, a rod includes a third hook disposed on a second end of the rod to stabilize the connection between the outrigger construct and the rib cage.

In one embodiment, the surgical system includes a distracting member configured for connection with a rib of a rib cage at a first end and a sliding connector at a second end. In one embodiment, a distracting member extends between a first end including a distracting hook and a second end including a distracting hook, both hooks being engageable with ribs of a rib cage. In one embodiment, at least two sliding connectors are connected to the rod and the distracting member. In one embodiment, the distracting hooks include inner surfaces disposed in opposite directions that are expandable to engage tissue of a rib cage.

In one embodiment, the surgical system includes a sliding connector having an open or closed attachment to the main construct configured to facilitate translation of the construct relative to the connector. In one embodiment, the connector includes a rib hook and a rod attachment configured for attaching to tissue of a rib cage. In one embodiment, a superior connector and an inferior connector are connected using a short section of a rod.

In one embodiment, the connector is connected to a head of a bone fastener, such as, for example, a bone screw at a first end and pivotally engaged to a rib hook at a second end.

In some embodiments, one or all of the components of the surgical system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, vessels, ligaments, tendons, cartilage and/or bone unless specifically referred to otherwise.

Figure 2:
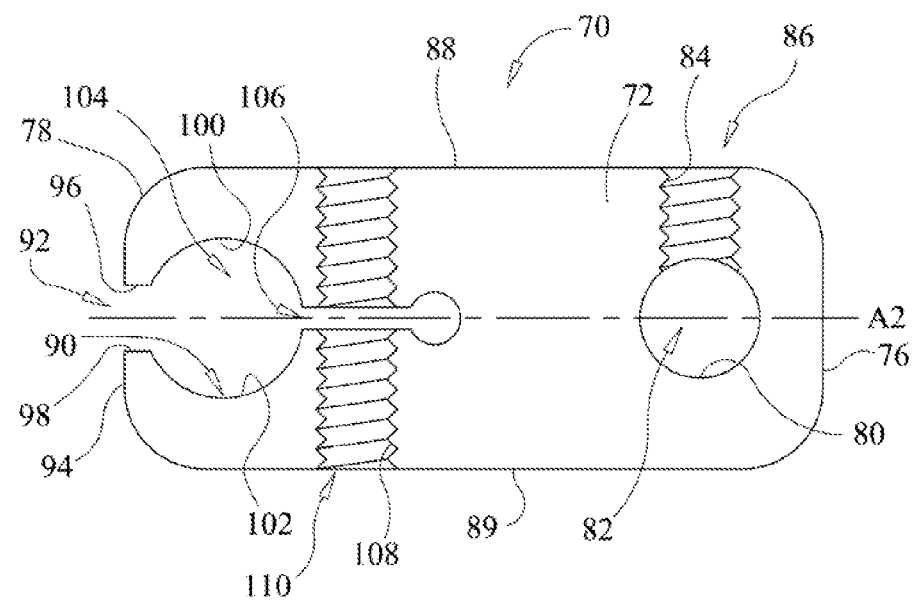
FIG. 2 is a side, cross-section view of a component of the system shown in FIG. 1.
Figure 3:
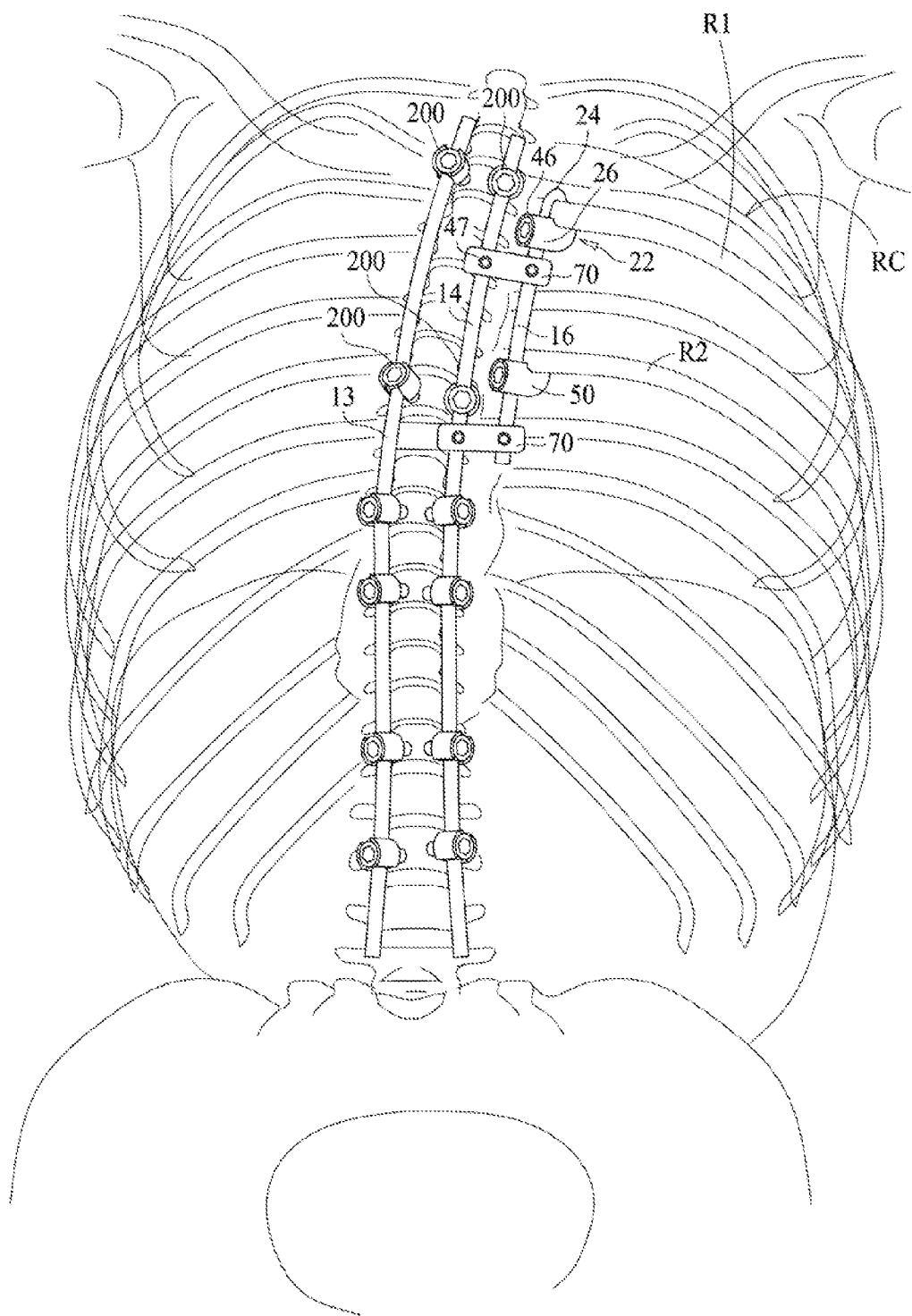
FIG. 3 is a plan view of components of one embodiment of a system in accordance with the principles of the present disclosure disposed with vertebrae.

The following discussion includes a description of a system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a system, such as, for example, a spinal correction system 10 in accordance with the principles of the present disclosure.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a spinal construct 12 that is configured for connecting to tissue, such as, for example, tissue of a rib cage and a spinal implant, such as, for example, a spinal rod 14 to correct a spinal deformity. Spinal construct 12 is configured for surgical implantation, as described herein, adjacent a scapula and muscle of a patient to resist and/or prevent spinal construct 12 from protruding and/or causing undesirable irritation to the patient, for example, through the skin of the patient. Spinal rod 14 defines an axis X along its length. In some embodiments, spinal construct 12 may be employed to treat an undesired curvature of a spine, such as scoliosis, while allowing for growth of the spinal column.

Spinal construct 12 includes a longitudinal element, such as, for example, a rod 16. In some embodiments, rod 16 has a first mating configuration, such as, for example, a non-circular cross section configuration to resist and/or prevent rotation of rod 16 relative to a sliding connector 70, as described herein. In some embodiments, rod 16 has alternate cross section configuration to resist and/or prevent rotation relative to sliding connector 70, such as, for example, hexagonal, oval, oblong, triangular, rectangular, square, polygonal, irregular, uniform, non-uniform, variable and/or tapered. Rod 16 extends between an end 18 and an end 20 defining a longitudinal axis A1 therebetween. Rod 16 includes a part 22 configured for connecting to tissue, such as, for example, a rib of a rib cage. Part 22 includes a hook 24 extending from end 18. Part 22 includes a hook 26 slidably engaged with rod 16 between ends 18, 20. In some embodiments, the longitudinal element can include one or a plurality of parts for connecting to tissue. In some embodiments, rod 16 has a circular cross section configuration.

Hook 24 includes a surface, such as, for example, an inner surface 28. Hook 26 includes a surface, such as, for example, an inner surface 30. In some embodiments, all or only a portion of inner surfaces 28, 30 may have alternate surface configurations, such as, for example, planar, rough, undulating, porous, semi-porous, dimpled, polished and/or textured. In some embodiments, inner surfaces 28, 30 may have an arcuate configuration configured to capture tissue of the rib cage therebetween. In some embodiments, hooks 24, 26 are variously configured, such as, for example, round, oval, oblong, irregular, uniform, non-uniform, consistent, variable, horseshoe shape, U-shape or kidney bean shape.

Hook 26 is configured for translation along rod 16 relative to hook 24 into a configuration for surfaces 28, 30 to engage with tissue of the rib cage. Hook 26 is moveable such that inner surfaces 28, 30 define an adjustable tissue cavity 32 configured for selective adjustability about the tissue of the rib cage. Tissue cavity 32 has a cross sectional area selectively adjustable to be substantially equal to a cross sectional area of a rib of the rib cage. Surface 28 is oriented in a first direction and surface 30 is oriented in a second, opposite direction such that inner surfaces 28, 30 face each other and are configured to engage opposite sides of an outer surface of a rib of a rib cage.

Hook 26 extends between an end 34 and an end 36. End 36 includes an inner surface 38 defining an inner passageway 40 configured for disposal of rod 16 such that rod 16 is axially translatable through inner passageway 40 and hook 26 is axially translatable relative to rod 16. End 36 includes a threaded inner surface 42 defining a passageway 44, extending transverse to and in communication with inner passageway 40. Passageway 44 is configured for disposal of a fastener, such as, for example, a set screw 46, as shown in FIG. 3. Set screw 46 is engageable with threaded inner surface 42 of hook 26 and an outer surface 48 of rod 16 such that hook 26 is detachably locked with rod 16 in a selected position along rod 16.

Rod 16 includes a part, such as, for example, a hook 50, similar to hooks 24, 26 described herein. Hook 50 is disposed adjacent end 20 of rod 16. Hook 50 extends between an end 52 and an end 54. End 52 includes an inner surface 56 defining a cavity 58 configured for disposal of tissue, such as, for example, a rib of a rib cage. In some embodiments, all or only a portion of inner surface 56 may have alternate surface configurations, such as, for example, planar, rough, undulating, porous, semi-porous, dimpled, polished and/or textured. In some embodiments, inner surface 56 may have an arcuate configuration configured to capture tissue of the rib cage. In some embodiments, hook 50 is variously configured, such as, for example, round, oval, oblong, irregular, uniform, non-uniform, consistent, variable, horseshoe shape, U-shape or kidney bean shape.

Inner surface 56 is oriented in the second direction or the same direction as inner surface 30 of hook 26. In some embodiments, inner surface 56 is oriented in the first direction or the same direction as inner surface 28 of hook 24.

End 54 includes an inner surface 60 defining a passageway 62 configured for disposal of rod 16 such that rod 16 is axially translatable through passageway 62 and hook 50 is axially translatable along longitudinal axis A1 relative to rod 16. End 54 includes a threaded inner surface 64 defining a passageway 66, extending transverse to and intersecting with passageway 62. Passageway 66 is configured for disposal of a fastener, such as, for example, a set screw (not shown), similar to set screw 46 described herein. The set screw is engageable with threaded inner surface 64 of hook 50 and outer surface 48 of rod 16 such that hook 50 is detachably lockable with rod 16 in a selected position along rod 16.

Spinal construct 12 includes a member, such as, for example, a sliding connector 70. Sliding connector 70 is connected with rod 16 and configured for connection with spinal rod 14 fixed with vertebrae to couple rod 16 with spinal rod 14. In some embodiments, spinal construct 12 includes a plurality of sliding connectors 70. Sliding connector 70 has a rectangular configuration and a thickness defined between a side wall 72 and a sidewall 74. In some embodiments, sliding connector 70 is variously configured, such as, for example, oval, oblong, triangular, rectangular, square, polygonal, irregular, uniform, non-uniform, variable and/or tapered. Sliding connector 70 extends between an end 76 and an end 78 defining a longitudinal axis A2 therebetween, substantially perpendicular to axis A1 of rod 16. In some embodiments, sliding connector 70 may be disposed at alternate orientations, relative to axis A1 of rod 16, such as, for example, transverse, and/or other angular orientations such as acute or obtuse, co-axial and/or may be offset or staggered.

End 76 includes an inner surface 80, as shown in FIG. 2, defining a cavity 82. Cavity 82 extends between side walls 72, 74 and is configured for sliding disposal of rod 16. In some embodiments, a second mating configuration, such as, for example, surface 80 engages a first mating configuration, such as, for example, an outer surface of rod 16 to resist and/or prevent rotation of rod 16 at the sliding engagement of the connection of rod 16 with connector 70. In some embodiments, cavity 82 has a cross section configuration corresponding to the cross sectional configuration of rod 16 to resist and/or prevent rotation of spinal rod 16 therein. Cavity 82 has a cross sectional area substantially equal to a cross sectional area of rod 16 such that rod 16 is axially translatable through cavity 82 relative to spinal rod 14 and sliding connector 70. Inner surface 80 includes a layer of friction-reducing material. In some embodiments, the layer may include an insert and/or coating comprising silicone, poly(tetrafluororthene), lubricants and/or material examples as described herein. The layer of friction-reducing material provides an even interface between inner surface 80 of sliding connector 70 and outer surface 48 of rod 16. In some embodiments, all or only a portion of inner surface 80 may have alternate surface configurations, such as, for example, planar, rough, undulating, porous, semi-porous, dimpled, polished and/or textured. Inner surface 80 defines a cavity 84. Cavity 84 includes a threaded passageway 86 extending from a surface 88 of sliding connector 70 into communication with cavity 82. Passageway 86 is configured for disposal of a fastener, such as, for example, a set screw (not shown) to selectively adjust the degree of friction between outer surface 48 of rod 16 and inner surface 80 of sliding connector 70. Axially translating the set screw through inner passage 86 engages the set screw with rod 16 to capture rod 16 in cavity 82.

End 78 includes an inner surface 90 defining a cavity 92 configured for disposal of spinal rod 14. Cavity 92 extends from a position between ends 76, 78 through a distalmost end surface 94 of end 78. Inner surface 90 includes a planar portion 96 and a planar portion 98. Portions 96, 98 are disposed in substantially parallel alignment with axis A2. Inner surface 90 includes an arcuate side 100 connected to planar portion 96 and an arcuate side 102 connected to planar portion 98. Sides 100, 102 define an arcuate opening 104 configured for disposal of spinal rod 14. In some embodiments, arcuate opening 104 is variously shaped, such as, for example, oval, oblong, rectangular, triangular, circular, square, polygonal, uniform, non-uniform, variable, tubular and/or tapered. In some embodiments, portions 96, 98 may be disposed in various alternative orientations relative to axis A2, such as, for example, relative angular orientations including acute or obtuse, offset and/or staggered and/or may be oriented in various planes of a body, such as, for example, coronal, sagittal and/or transverse. In some embodiments, portions 96, 98 may be disposed in various alternative orientations relative to arcuate sides 100, 102, such as, for example, those described herein. Inner surface 90 defines a slot 106 extending from arcuate opening 104 having a keyhole configuration. Slot 106 is configured to facilitate expansion of arcuate opening 104. In some embodiments, slot 106 is variously configured, such as, for example, those alternatives described herein, to facilitate expansion of arcuate opening 104. Arcuate opening 104 is expandable to receive spinal rod 14 such that inner surface 90 slidably captures spinal rod 14. End 78 is configured to expand such that portions 96, 98 move apart to allow a spinal rod 14 to be inserted into end 78 and be captured by arcuate sides 100, 102, as discussed herein.

Sliding connector 70 includes a threaded inner surface 108 defining an inner passageway 110. Inner passageway 110 extends transverse to cavity 92, through a width of sliding connector 70 defined between surface 88 and a surface 89 of sliding connector 70. Inner passageway 110 intersects slot 106 and is configured for disposal of a set screw 47, as shown in FIG. 3, to selectively adjust a cross sectional area of arcuate opening 104, as described herein. Axially translating set screw 47 through inner passageway 110 contracts or reduces the cross sectional area of arcuate opening 104 to resist and/or prevent sliding connector 70 from disengaging spinal rod 14. Sliding connector 70 is disposed in a side-by-side orientation between spinal rod 14 and longitudinal element 16 to couple longitudinal element 16 with spinal rod 14.

System 10 includes spinal rod 14. Spinal rod 14 is substantially cylindrical. In one embodiment, spinal rod 14 is disposed to extend along an axial plane, such as for example, a sagittal plane of a body of a patient. In some embodiments, system 10 may include one or a plurality of spinal implants 14. In some embodiments, one or all of a plurality of spinal implants 14 may be disposed in various relative orientations, such as, for example, side-by-side, parallel, transverse, perpendicular or angular and/or be disposed to extend along substantially coronal, sagittal and transverse planes of a body.

Spinal rod 14 has a uniform thickness/diameter. In some embodiments, spinal rod 14 may have various surface configurations, such as, for example, rough, threaded for connection with surgical instruments, arcuate, undulating, porous, semi-porous, dimpled, polished and/or textured. In some embodiments, the thickness defined by spinal rod 14 may be uniformly increasing or decreasing, or have alternate diameter dimensions along its length. In some embodiments, spinal rod 14 may have various cross section configurations, such as, for example, oval, oblong, triangular, rectangular, square, polygonal, irregular, uniform, non-uniform, variable and/or tapered. In some embodiments, spinal rod 14 may extend in various configurations, such as, for example, linear, arcuate, curved, angular and/or pre-bent according to a selected configuration of vertebrae.

In some embodiments, spinal rod 14 may have various lengths. In some embodiments, spinal rod 14 may be made from autograft and/or allograft and be configured for resorbable or degradable applications. In one embodiment, spinal rod 14 is a cadaver tendon. In one embodiment, spinal rod 14 is a tendon that may be harvested, for example, from a patient or donor. In some embodiments, all or only a portion of spinal rod 14 may have a semi-rigid, flexible or elastic configuration and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. In one embodiment, spinal rod 14 provides a selective amount of expansion and/or extension in an axial direction. In some embodiments, spinal rod 14 may have a flexible configuration, which includes movement in a lateral or side to side direction. In some embodiments, spinal rod 14 may be compressible in an axial direction. Spinal rod 14 can include a plurality of separately attachable or connectable portions or sections, such as bands or loops, or may be monolithically formed as a single continuous element.

System 10 includes a plurality of bone fasteners 200 configured for disposal with tissue, such as, for example, a vertebral body, and engageable with spinal rod 14. Bone fasteners 200 include a head configured for attachment with spinal rod 14, and an elongated shaft configured for penetrating tissue. The head includes a pair of spaced apart arms defining a U-shaped implant cavity. The elongated shaft of bone fastener 200 is configured with a cylindrical cross section and includes an outer surface having an external thread form. In some embodiments, the external thread form may include a single thread turn or a plurality of discrete threads. In some embodiments, other engaging structures may be disposed on the shaft, such as, for example, a nail configuration, barbs, expanding elements, raised elements and/or spikes to facilitate engagement of the shaft with tissue, such as, for example, vertebrae.

In some embodiments, all or only a portion of the shaft may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of the shaft may be disposed at alternate orientations, relative to a longitudinal axis of bone fastener 200, such as, for example, transverse, perpendicular and/or other angular orientations such as acute or obtuse, co-axial and/or may be offset or staggered. In some embodiments, all or only a portion of the shaft may be cannulated.

In some embodiments, the shaft may be made for attachment to bone, such as cervical, thoracic, lumbar and or sacral vertebral bone structures, or other tissues. In one embodiment, the shaft may be a screw, or could also be alternatively configured, for example, as a vertebral hook or clamp. In some embodiments, the threads may be self-tapping or intermittent, or may have more than one crest winding about the shaft. In one embodiment, the outer surface may include an opening for accommodating a tool (not shown) for gripping or turning the bone fastener 200.

In some embodiments, one or more of fasteners 200 may be engaged with tissue in various orientations, such as, for example, series, parallel, offset, staggered and/or alternate vertebral levels. In some embodiments, one or more of fasteners 200 may comprise multi-axial screws, sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In operation, spinal construct 12 is disposed adjacent, for example, beneath a scapula of a patient and beneath a muscle mass to prevent spinal construct 12 from protruding through the skin of the patient. A practitioner manipulates spinal construct 12 to fix and/or attach spinal construct 12 with tissue, such as, for example, a rib R1 of a rib cage RC and spinal rod 14 fixed with vertebrae V, as shown in FIG. 3. Sliding connector 70 is positioned such that portions 96, 98 are disposed in contact with spinal rod 14. A force is applied to sliding connector 70, in the direction shown by arrow A in FIG. 1, causing portions 96, 98 to translate over spinal rod 14 and fit around spinal rod 14 such that spinal rod 14 is disposed and provisionally locked within arcuate opening 104. An outer surface 15 of spinal rod 14 engages arcuate sides 100, 102 of inner surface 90 such that spinal rod 14 is disposed in arcuate opening 104 of sliding connector 70 and connector 70 can be translated along spinal rod 14 to a desired position. Set screw 47, as shown in FIG. 3, is axially translated through inner passageway 110 to draw portions 96, 98 together collapsing arcuate opening 104 such that portions 96, 98 resist and/or prevent the disengagement of spinal rod 14 from arcuate opening 104.

Rod 16 is translated along longitudinal axis A1 through cavity 82 of sliding connector 70 to engage inner surface 28 of hook 24 with tissue, such as, for example, rib R1 of rib cage RC. Hook 26 is translated along rod 16 to selectively adjust tissue cavity 32 and engage inner surface 30 of hook 26 with rib R1 such that part 22 is connected with rib R1. Rib R1 is captured between hooks 24 and 26 in tissue cavity 32. A set screw is axially translated through inner passageway 11 into engagement with rod 16 such that hook 26 is releasably locked with rod 16.

Hook 50 is translated along rod 16 to engage inner surface 56 of hook 50 with tissue, such as, for example, a rib R2 of rib cage RC. A set screw is axially translated through inner passageway 66 into engagement with rod 16 such that hook 50 is releasably locked with rod 16 to resist and/or prevent relative movement between rod 16 and rib cage RC.

In assembly, operation and use, a spinal correction system 10, similar to the systems described herein, is employed with a surgical correction procedure. For example, spinal correction system 10 may be employed in surgical procedures for treating disorders of the spine, such as, for example, undesirable curvatures of a spine of a child or adolescent requiring a dynamic spinal stabilization system to accommodate a growing spinal column.

In some embodiments, one or all of the components of spinal correction system 10 can be delivered or implanted as a pre-assembled device or can be assembled in situ. The components of spinal correction system 10 may be completely or partially revised, removed or replaced. For example, spinal correction system 10 can be employed with a surgical correction treatment of an applicable condition or injury of an affected section of a spinal column and adjacent areas within a body, such as, for example, vertebrae V, as shown in FIG. 3.

In use, to treat a selected section of vertebrae V, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Bone fasteners 200 are delivered along the surgical pathway to a surgical site that includes vertebrae V. Bone fasteners 200 are delivered adjacent vertebrae V. The shafts of bone fasteners 200 are oriented with the bony anatomy of vertebrae V and a driver (not shown) is manipulable to drive, torque, insert or otherwise fasten bone fasteners 200 to vertebrae V.

Spinal rod 14 and a spinal rod 13, similar to spinal rod 14, are delivered along the surgical pathway to the surgical site adjacent vertebrae V. In some embodiments, spinal rods 13, 14 and spinal construct 12 and/or bone fasteners 200 can be delivered or implanted as pre-assembled components or can be assembled in situ. Spinal rods 13, 14 are positioned for disposal within the U-shaped implant cavity of bone fasteners 200 to connect spinal rods 13, 14 with bone fasteners 200. In some embodiments, spinal rods 13, 14 may be attached with vertebrae V with a plurality of bone fasteners 200 over a plurality of vertebral levels. Spinal rods 13, 14 are implanted in a side-by-side orientation along vertebrae V in a bi-lateral configuration with vertebrae V, as shown in FIG. 3, such that spinal rod 14 is disposed with a lateral side and spinal rod 13 is disposed with a contra-lateral side. In some embodiments, spinal rods 13, 14 are oriented in various configurations, as described herein. In some embodiments, only spinal rod 13 or only spinal rod 14 is implanted with vertebrae V such that the implanted spinal rod is disposed in a uni-lateral configuration with vertebrae V.

Set screws are torqued and threaded with threads of the U-shaped implant cavity of selected bone fasteners 200 disposed cephalad and caudal to an apical curvature abnormality to secure spinal rod 14 with vertebrae V. The set screws capture spinal rod 14 within the U-shaped implant cavity of bone fasteners 200 without fixing spinal rod 14 relative to bone fasteners 200 disposed cephalad and caudal to the apical curvature such that longitudinal spinal growth of selected sections of vertebrae is allowed. In some embodiments, set screws are torqued and threaded with threads of the U-shaped implant cavity of selected bone fasteners 200 disposed adjacent the apical curvature abnormality to fix spinal rod 14 with bone fasteners 200 such that bone fasteners 200 disposed adjacent the apical curvature abnormality resist relative movement of spinal rod 14.

Spinal construct 12 is surgically implanted beneath the scapula of the patient and beneath muscle mass to prevent spinal construct 12 from protruding through skin of the patient. A practitioner manipulates spinal construct 12 to fix and/or attach spinal construct 12 with R1 of a rib cage RC and spinal rod 14 fixed with vertebrae V in a uni-lateral configuration. In some embodiments, a plurality of spinal constructs 12 are implanted with the patient and connected with spinal rod 14 and spinal rod 13 in a bilateral configuration with vertebrae V and rods 13, 14. Sliding connector 70 is positioned such that portions 96, 98 are disposed in contact with spinal rod 14. A force is applied to sliding connector 70 such that portions 96, 98 translate over spinal rod 14 and outer surface 15 of spinal rod 14 engages arcuate sides 100, 102 of inner surface 90. Spinal rod 14 is provisionally locked within arcuate opening 104 and portions 96, 98 prevent spinal rod 14 from disengaging from arcuate opening 104 during translation of connector 70 along spinal rod 14. Set screw 47 is axially translated through inner passageway 110 to draw portions 96, 98 together collapsing arcuate opening 104 such that portions 96, 98 resist and/or prevent the disengagement of spinal rod 14 from arcuate opening 104.

Rod 16 is translated along longitudinal axis A1 through cavity 82 of sliding connector 70 to engage inner surface 28 of hook 24 with tissue, such as, for example, rib R1 of rib cage RC. Hook 26 is translated along rod 16 to selectively adjust tissue cavity 32 and engage inner surface 30 of hook 26 with rib R1 such that part 22 is connected with rib R1. Rib R1 is captured between hooks 24, 26 in tissue cavity 32. A set screw is axially translated through inner passageway 44 into engagement with rod 16 such that hook 26 is releasably locked to rod 16.

Hook 50 is translated along rod 16 to engage inner surface 56 of hook 50 with rib R2 of rib cage RC. A set screw is axially translated through inner passageway 66 into engagement with rod 16 such that hook 50 is releasably locked to rod 16 to resist and/or prevent relative movement between rod 16 and rib cage RC.

In some embodiments, spinal correction system 10 may include a spinal construct comprising one or a plurality of spinal constructs 12 that are each attachable with a selected vertebral level of vertebrae V, or two or more selected vertebral levels of vertebrae V. Spinal correction system 10 accommodates growth of vertebrae of a selected section of the spine for a correction treatment to treat various spine pathologies, such as, for example, adolescent idiopathic scoliosis and Scheuermann's kyphosis.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal correction system 10 are removed and the incision is closed. Spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

Figure 4:
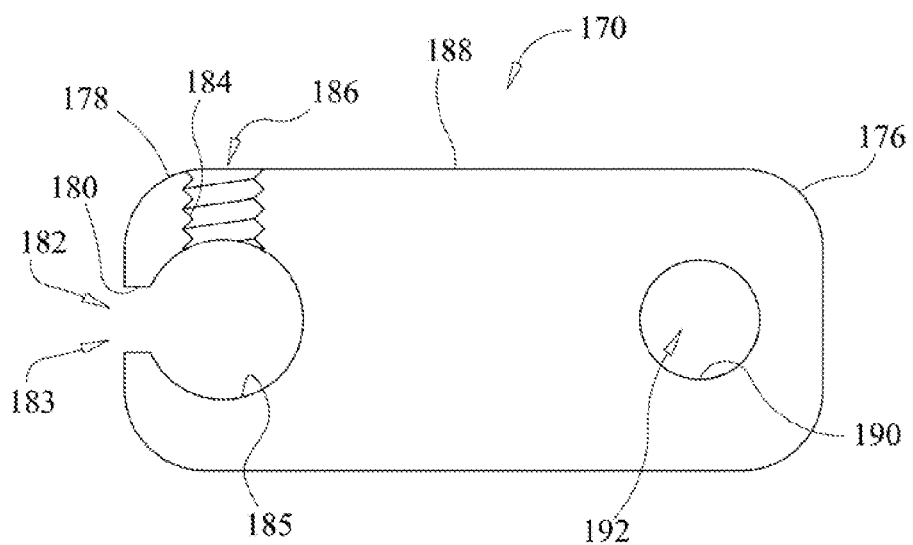
FIG. 4 is a side, cross section view of a component of one embodiment of the system shown in FIG. 1.

In one embodiment, as shown in FIG. 4, spinal correction system 10, similar to the systems and methods described with regard to FIGS. 1-3, includes spinal construct 12. Spinal construct 12 includes a sliding connector 170, similar to sliding connector 70 described with regard to FIGS. 1-3. Sliding connector 170 extends between an end 176 and an end 178. End 176 includes an arcuate cutout 180 defining a cavity 182 configured for disposal of spinal rod 14. Cavity 182 has a C-shaped configuration to allow for the insertion of spinal rod 14 into cavity 182. In some embodiments, cavity 182 is variously configured, such as, for example, those alternatives described herein. Cavity 182 has an angled opening 183 having a sloped portion 185 configured to provisionally lock spinal rod 14 within cavity 182 as it translates over sloped portion 185. Sliding connector 170 includes an inner threaded surface 184 defining an inner passageway 186. Inner passageway 186 extends transverse to cavity 182, between and through surface 188 and inner surface 180. Axially translating a set screw (not shown) through inner passageway 186 engages the set screw with spinal rod 14 to capture spinal rod 14 in cavity 182. End 176 includes an inner surface 190 defining an enclosed opening 192 configured for disposal of rod 16 such that rod 16 is axially translatable through enclosed opening 192 relative to sliding connector 170. In one embodiment, enclosed opening 192 may have a circular configuration. In some embodiments, all or only a portion of the enclosed opening 192 may have alternate configurations, such as, for example, oval, oblong, triangular, square, polygonal, irregular, uniform, non-uniform, arcuate, variable and/or tapered.

Figure 5:
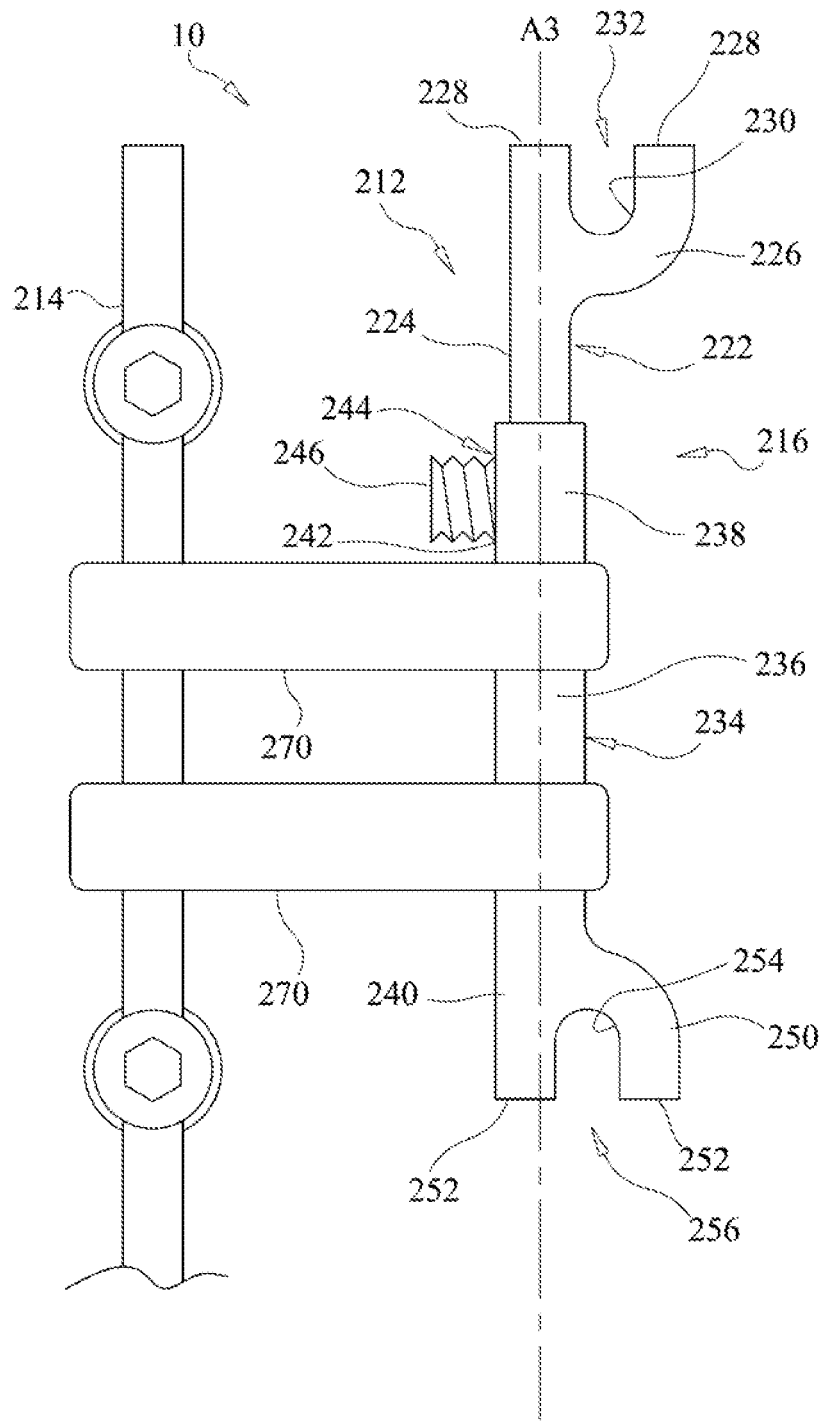
FIG. 5 is a plan view of components of one embodiment of a system in accordance with the principles of the present disclosure.

In one embodiment, as shown in FIG. 5, spinal correction system 10, similar to the systems and methods described herein, includes a spinal construct 212, similar to spinal construct 12 described herein. Spinal construct 212 is configured for connecting to tissue of a rib cage and a spinal implant 214, similar to spinal rod 14 described herein, to correct a spinal deformity, such as, for example, an undesirable curvature of a spine of a child or adolescent while allowing for longitudinal growth of the spinal column.

Spinal construct 212 includes a longitudinal element 216 defining a longitudinal axis A3. Longitudinal element 216 includes at least one part, such as, for example, a part 222. Part 222 includes an elongate member 224 and a distracting hook 226 extending therefrom configured for engagement with a first rib of a rib cage. Elongate member 224 is slidably disposed in a sleeve 236 of a part 234, as described herein. Distracting hook 226 includes a pair of spaced apart arms 228 including an inner surface 230 oriented in a first direction. Arms 228 define a cavity 232 having an arcuate configuration configured for disposal of the rib.

Longitudinal element 216 includes part 234. Part 234 includes sleeve 236 having circular cross sectional configuration configured for slidable disposal of part 222. In some embodiments, all or only a portion of the sleeve may have alternate cross section configurations, such as, for example, oval, oblong, triangular, square, polygonal, irregular, uniform, non-uniform, offset, staggered, undulating, arcuate, variable and/or tapered. Sleeve 236 extends between an end 238 and an end 240. End 238 includes an inner surface 242 defining a passageway 244 configured for disposal of a set screw 246. Part 234 includes a distracting hook 250, similar to distracting hook 226 described herein, configured for connecting to a second rib of the rib cage, which is spaced apart one or a plurality of ribs from the first rib. Distracting hook 226 is axially movable relative to distracting hook 250. Distracting hook 250 extends from end 240. Distracting hook 250 includes a pair of spaced apart arms 252 including an inner surface 254 oriented in a second direction, opposite the direction of inner surface 230 of distracting hook 226. Arms 252 define a cavity 256 having an arcuate configuration configured for disposal of the second rib.

Spinal construct 212 includes a pair of sliding connectors 270, similar to sliding connector 70, described herein with regard to FIGS. 1-3. In some embodiments, spinal construct 212 includes one sliding connector. Sliding connectors 270 are disposed in a side-by-side orientation between spinal implant 214 and longitudinal element 216 to couple longitudinal element 216 with spinal implant 214.

In operation, longitudinal element 216 is axially translated relative to spinal implant 214 such that distracting hook 250 engages the second rib to capture the second rib between arms 252 in cavity 256. Part 222 is axially translated within sleeve 236 such that distracting hook 226 engages the first rib to capture the first rib between arms 228 in cavity 232. Set screw 246 is axially translated through passageway 244 into engagement with elongate member 224 such that part 222 is detachably locked relative to part 234 fixing longitudinal element 216 between the first and second ribs.

Figure 6:
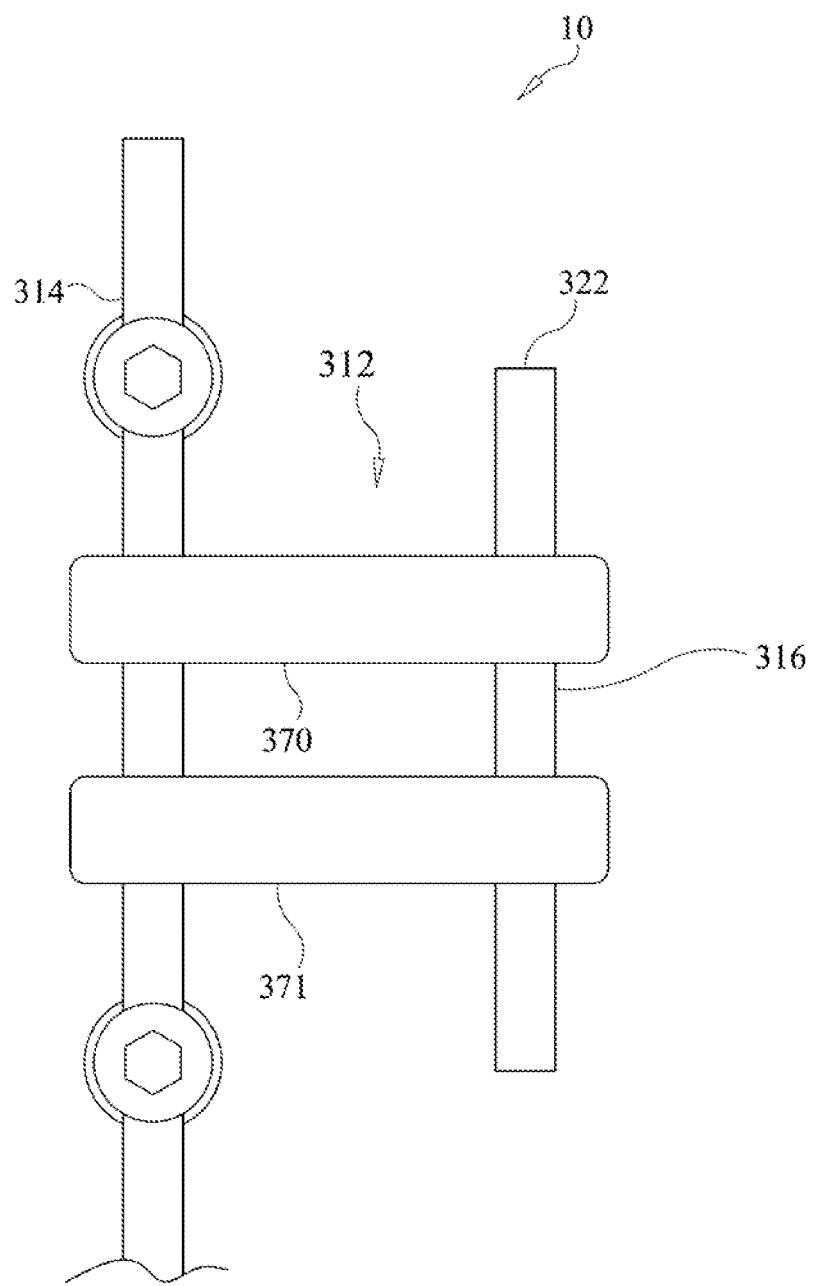
FIG. 6 is a plan view of components of one embodiment system of a system in accordance with the principles of the present disclosure.
Figure 7:
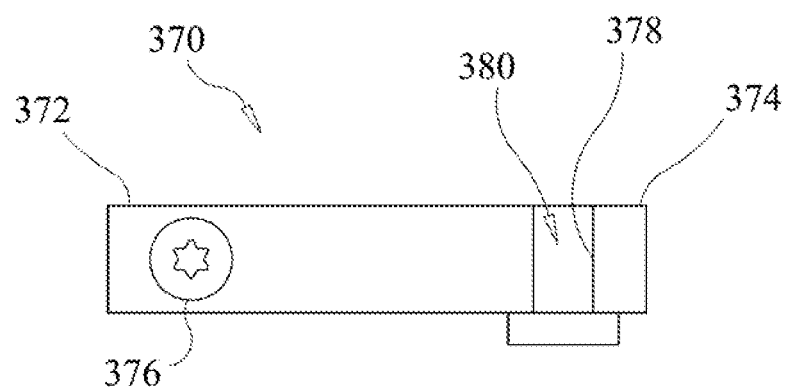
FIG. 7 is a side view of components of the system shown in FIG. 6.
Figure 8:
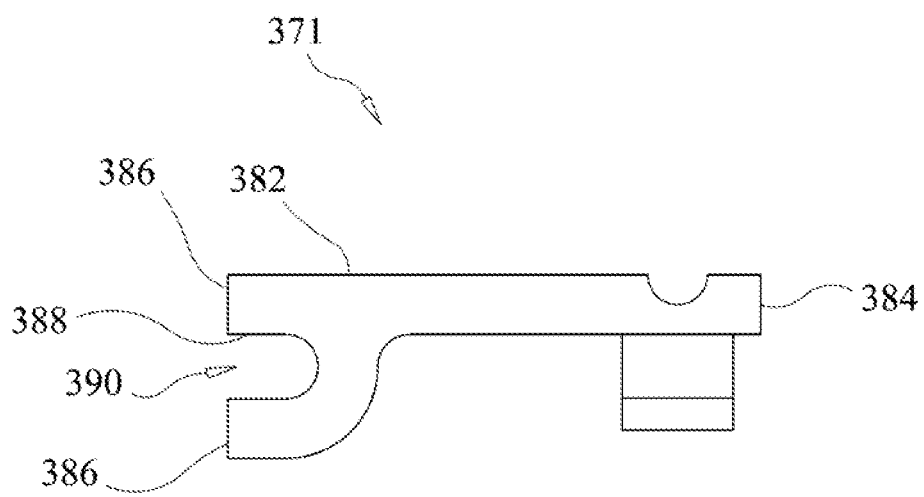
FIG. 8 is a plan view of components of the system shown in FIG. 6.

In one embodiment, as shown in FIGS. 6-8, spinal correction system 10, similar to the systems and methods described herein, includes a spinal construct 312, similar to spinal construct 12 described herein. Spinal construct 312 is configured for connecting to tissue of a rib cage and a spinal implant 314, similar to spinal rod 14 described herein, to correct a spinal deformity, such as, for example, those described herein.

Spinal construct 312 includes a longitudinal element 316. Longitudinal element 316 includes at least one part 322, similar to part 22 described herein, configured for connecting to tissue of a rib cage. Spinal construct 312 includes members, such as, for example, a sliding connector 370 and a sliding connector 371 similar to sliding connector 70 described herein. Sliding connectors 370, 371 are disposed in a side-by-side orientation between spinal implant 314 and longitudinal element 316. Sliding connectors 370, 371 are slidably engaged to spinal implant 314 such that spinal implant 314 is translatable relative to sliding connectors 370, 371. In some embodiments, sliding connectors 370, 371 are slidably engaged to longitudinal element 316 such that longitudinal element 316 is translatable relative to sliding connectors 370, 371.

Sliding connector 370, as shown in FIG. 7, extends between an end 372 and an end 374. End 372 includes an enclosed opening 376 configured for disposal of spinal implant 314. In one embodiment, enclosed opening 376 may have a circular configuration. In some embodiments, all or only a portion of the enclosed opening 376 may have alternate configurations, such as, for example, oval, oblong, triangular, square, polygonal, irregular, uniform, non-uniform, arcuate, variable and/or tapered. End 374 includes an inner surface 378 defining a passageway 380 configured for disposal of longitudinal element 316. Sliding connector 371, as shown in FIG. 8, extends between an end 382 and an end 384. End 382 includes a pair of spaced apart arms 386 having an inner surface 388. Arms 386 define an arcuate cavity 390 configured for disposal of spinal implant 314. In some embodiments, cavity 390 is variously configured, such as, for example, those alternatives described herein.

Figure 9:
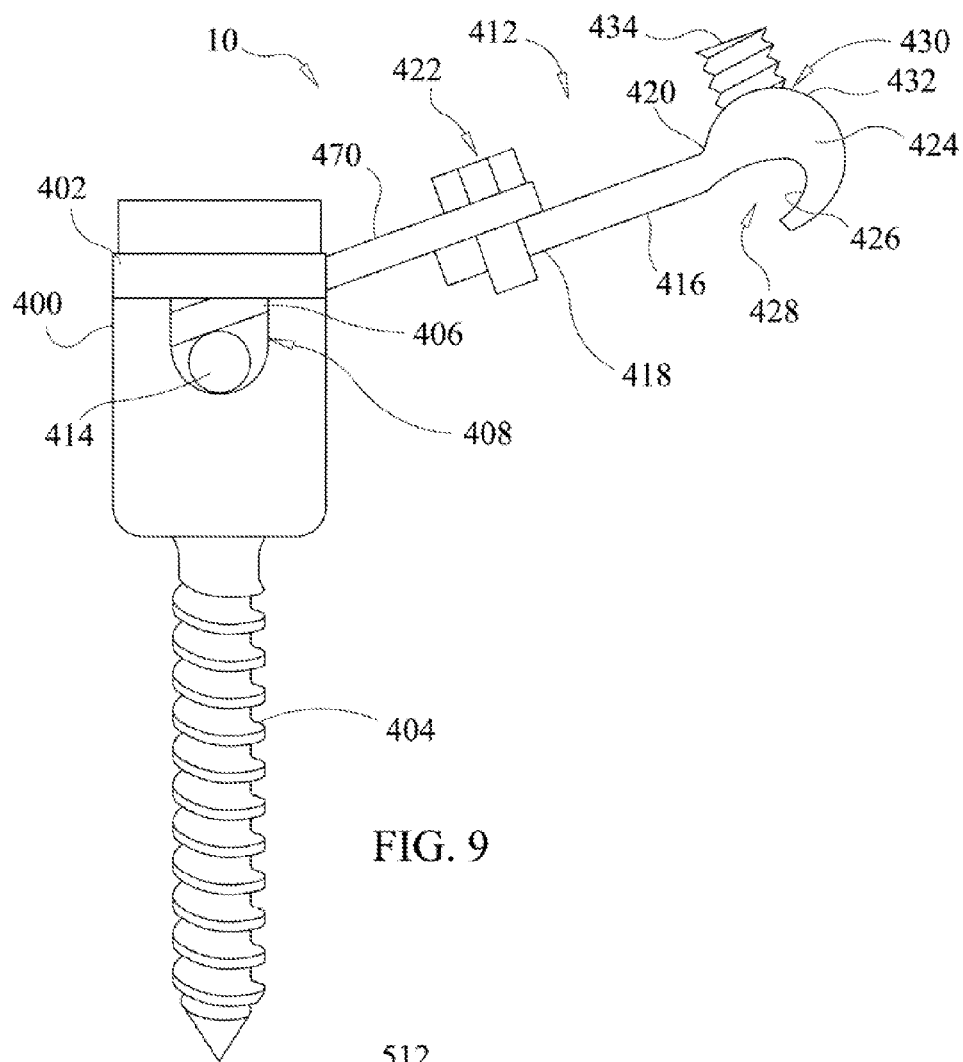
FIG. 9 is a side view of components of one embodiment of a system in accordance with the principles of the present disclosure.

In one embodiment, as shown in FIG. 9, spinal correction system 10, miler to the systems and methods described herein, includes a spinal construct 412, similar to spinal construct 12 described herein. Spinal construct 412 is configured for connecting to tissue of a rib cage and a spinal implant, such as, for example, a bone fastener 400 as described herein, to correct a spinal deformity, such as, for example, those described herein.

Spinal construct 412 includes a longitudinal element 416 extending between an end 418 and an end 420. End 418 is pivotally connected to a member 470 via a nut and bolt assembly 422. End 420 includes a hook 424, similar to hook 24 described herein, configured for engagement with tissue, such as, for example, a rib of a rib cage. Hook 424 includes an inner surface 426 defining a tissue cavity 428. Hook 424 includes an inner passageway 430 extending from an outer surface 432 of hook 424 through inner surface 426 configured for disposal of a set screw 434. Set screw 434 is axially translated through inner passageway 430 into cavity 428 to capture tissue of a rib cage between inner surface 426 and set screw 434.

Spinal construct 412 includes member 470. Member 470 is pivotally connected with end 418 of longitudinal element 416 and configured for connection with bone fastener 400 fixed with vertebrae. Member 470 connects with a head 402 of bone fastener 400, as described herein. System 10 includes bone fastener 400, similar to bone fastener 200 described herein, configured for fixation with bony anatomy of vertebrae. Fastener 400 includes a head 402 and a shaft 404 configured for penetrating tissue. Head 402 includes an inner surface 406 defining a U-shaped implant cavity 408 configured for disposal of a spinal implant 414, similar to spinal rod 14 described herein.

Figure 10:
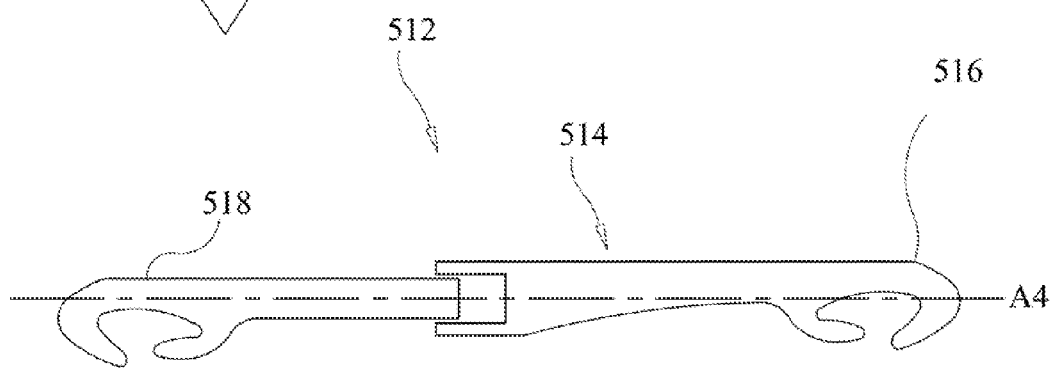
FIG. 10 is a side view of components of one embodiment of a system in accordance with the principles of the present disclosure.

In one embodiment, as shown in FIG. 10, spinal correction system 10, similar to the systems and methods described herein, includes a spinal construct 512, similar to spinal construct 12 described herein. Spinal construct 512 is configured for connecting to tissue of a rib cage and a spinal implant, such as, for example, those described herein, to correct a spinal deformity, such as, for example, those described herein. Spinal construct 512 includes a longitudinal element, such as, for example, a rod 514 defining an axis A4. Rod 514 includes parts, such as, for example, a hook 516 and a hook 518, similar to hook 24 described herein, configured for engagement with tissue, such as, for example, ribs of a rib cage. Hooks 516, 518 are engaged in a telescoping configuration such that hooks 516, 518 are axially translatable relative to one another along axis A4 and between at least two ribs of the rib cage. In some embodiments, hooks 516, 518 are engaged to one another in alternative configurations, such as, for example, slidingly engaged, an interlocking engagement, or integrally formed with a flexible connection, to provide for relative axial movement between hooks 516, 518.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a longitudinal element comprising an end having a first hook configured for connecting to a rib cage;
   at least one part slidably connected with the longitudinal element and configured for connecting to tissue of the rib cage, the at least one part comprising a second hook; and
   a member connected with the longitudinal element and configured for connection with a spinal implant fixed with vertebrae, wherein the member comprises opposite top and bottom surfaces and opposite first and second side surfaces that each extend between the top and bottom surfaces, the member comprising opposite distal and proximal end surfaces that each extend between the top and bottom surfaces and the side surfaces, the member further comprising a cavity that extends through the side surfaces and a slot that is in communication with the cavity, the cavity having the spinal implant positioned therein, the cavity comprising an opening that extends through the distal end surface, the opening being defined by a first portion and a second portion that faces the first portion, the cavity being expandable between a first configuration in which the portions are spaced apart a first distance and a second configuration in which the portions are spaced apart a second distance that is greater than the first distance.

2. A spinal construct as recited in claim 1, wherein the second hook is movable relative to the first hook in a configuration for connection with the tissue of the rib cage.

3. A spinal construct as recited in claim 2, wherein the first and second hooks define an adjustable tissue cavity.

4. A spinal construct as recited in claim 3, wherein the cavity is selectively adjustable about the tissue.

5. A spinal construct as recited in claim 1, wherein the at least one part comprises a first part the second hook oriented in a first direction and a second part including that is spaced apart from the first part and includes a third hook oriented in the first direction.

6. A spinal construct as recited in claim 5, wherein the first hook is oriented in a second direction that is opposite the first direction.

7. A spinal construct as recited in claim 5, wherein the first and second parts are slidable along a length of the longitudinal element.

8. A spinal construct as recited in claim 5, wherein:
   the first and second parts are slidable along a length of the longitudinal element; and
   the first hook defines a cavity that faces a cavity defined by the second hook.

9. A spinal construct as recited in claim 1, wherein the longitudinal element includes a mating surface having a non-circular cross section configuration.

10. A spinal construct as recited in claim 1, wherein the member extends between a first end engageable with the spinal implant and a second end slidably engaged with the longitudinal element.

11. A spinal construct as recited in claim 1, wherein the first hook is monolithically formed with the end such that the first hook is permanently fixed relative to the end.

12. A spinal construct comprising:
a longitudinal element comprising an end having a first hook configured for connecting to a rib cage, the first hook being permanently fixed to the end;
a first part connected to the longitudinal element such that the first part is slidable along a length of the longitudinal element, the first part including a second hook oriented in a first direction;
a second part connected to the longitudinal element such that the second part is slidable along a length of the longitudinal element, the second part including a third hook oriented in the first direction; and
a member connected with the longitudinal element and configured for connection with a spinal implant fixed with vertebrae, the member comprising a first cavity having a circular cross sectional configuration, the longitudinal element being positioned within the first cavity to connect the member with the longitudinal element, the member further comprising a second cavity having the spinal implant positioned therein, wherein a slot extends from a first side of the second cavity and an opening extends from an opposite second side of the second cavity, the opening being defined by a first portion and a second portion that faces the first portion, the second cavity being movable between a first configuration in which the portions are spaced apart a first distance and a second configuration in which the portions are spaced apart a second distance that is greater than the first distance.

13. A spinal construct comprising:
a longitudinal element comprising an end having a first hook configured for connecting to a rib cage;
at least one part slidably connected with the longitudinal element and configured for connecting to tissue of the rib cage, the at least one part comprising a second hook; and
a member connected with the longitudinal element and configured for connection with a spinal implant fixed with vertebrae,
wherein the member comprises a cavity having the spinal implant positioned therein, a slot extending from a first side of the cavity and an opening extending from an opposite second side of the cavity, the opening being defined by a first portion and a second portion that faces the first portion, the member comprising a threaded passageway that extends through the top and bottom surfaces and the slot, the spinal construct comprising a set screw positioned in the threaded passageway, the set screw being movable between a first configuration in which the portions are spaced apart a first distance and a second configuration in which the portions are spaced apart a second distance that is greater than the first distance.

* * * * *

UNITED STATES PATENT AND TRADEMARK OFFICE
CERTIFICATE OF CORRECTION

PATENT NO.           : 9,486,252 B2
APPLICATION NO.      : 14/151042
DATED                : November 8, 2016
INVENTOR(S)          : McCarthy et al.

It is certified that error appears in the above-identified patent and that said Letters Patent is hereby corrected as shown below:

On the Title Page

Item (72), under "Inventors", in Column 1, Line 1, delete "Richard E McCarthy," and insert -- Richard E. McCarthy, --, therefor.

In the Specification

In Column 1, Line 27, delete "such as" and insert -- such as, --, therefor.

In Column 2, Lines 4-5, delete "embodiment system of a" and insert -- embodiment of a --, therefor.

In Column 10, Lines 47-48, delete "passageway 11" and insert -- passageway 44 --, therefor.

In Column 13, Line 43, delete "circular'" and insert -- circular --, therefor.

In Column 14, Line 53, delete "connector 371" and insert -- connector 371, --, therefor.

In Column 15, Line 14, delete "miler" and insert -- similar --, therefor.

In the Claims

In Column 16, Line 35, in Claim 2, delete "A spinal" and insert -- The spinal --, therefor.

In Column 16, Line 38, in Claim 3, delete "A spinal" and insert -- The spinal --, therefor.

In Column 16, Line 40, in Claim 4, delete "A spinal" and insert -- The spinal --, therefor.

In Column 16, Line 42, in Claim 5, delete "A spinal" and insert -- The spinal --, therefor.

Signed and Sealed this
Third Day of January, 2017

Michelle K. Lee
*Director of the United States Patent and Trademark Office*

CERTIFICATE OF CORRECTION (continued)
U.S. Pat. No. 9,486,252 B2

In Column 16, Line 43, in Claim 5, delete "part the" and insert -- part including the --, therefor.

In Column 16, Line 44, in Claim 5, delete "part including that" and insert -- part that --, therefor.

In Column 16, Line 47, in Claim 6, delete "A spinal" and insert -- The spinal --, therefor.

In Column 16, Line 50, in Claim 7, delete "A spinal" and insert -- The spinal --, therefor.

In Column 16, Line 53, in Claim 8, delete "A spinal" and insert -- The spinal --, therefor.

In Column 16, Line 58, in Claim 9, delete "A spinal" and insert -- The spinal --, therefor.

In Column 16, Line 61, in Claim 10, delete "A spinal" and insert -- The spinal --, therefor.

In Column 16, Line 65, in Claim 11, delete "A spinal" and insert -- The spinal --, therefor.